US006982328B2

(12) United States Patent
Werpy et al.

(10) Patent No.: US 6,982,328 B2
(45) Date of Patent: Jan. 3, 2006

(54) METHODS OF PRODUCING COMPOUNDS FROM PLANT MATERIAL

(75) Inventors: Todd A. Werpy, West Richland, WA (US); Andrew J. Schmidt, Richland, WA (US); John G. Frye, Jr., Richland, WA (US); Alan H. Zacher, Kennewick, WA (US); James A. Franz, Kennewick, WA (US); Mikhail S. Alnajjar, Richland, WA (US); Gary G. Neuenschwander, Burbank, WA (US); Eric V. Alderson, Kennewick, WA (US); Rick J. Orth, Kennewick, WA (US); Charles A. Abbas, Champaign, IL (US); Kyle E. Beery, Decatur, IL (US); Anne M. Rammelsberg, Decatur, IL (US); Catherine J. Kim, Decatur, IL (US)

(73) Assignees: Archer Daniels Midland Company, Decatur, IL (US); Battelle Memorial Institute, Richland, WA (US)

( * ) Notice: Subject to any disclaimer, the term of this patent is extended or adjusted under 35 U.S.C. 154(b) by 85 days.

(21) Appl. No.: 10/379,299

(22) Filed: Mar. 3, 2003

(65) Prior Publication Data

US 2004/0175806 A1 Sep. 9, 2004

(51) Int. Cl.
*C07H 1/06* (2006.01)
*C07H 1/08* (2006.01)
*C08B 37/14* (2006.01)
*C08B 30/04* (2006.01)

(52) U.S. Cl. ............... 536/128; 536/124; 536/56; 536/102; 536/123.1

(58) Field of Classification Search ............ 536/128, 536/124, 56, 102, 123.1, 1

See application file for complete search history.

(56) References Cited

U.S. PATENT DOCUMENTS

| 4,038,481 A |   | 7/1977  | Antrim et al. |
| 4,239,906 A |   | 12/1980 | Antrim et al. |
| 4,476,331 A | * | 10/1984 | Dubeck et al. ............ 568/861 |
| 4,689,409 A | * | 8/1987  | Reeve et al. ............... 536/102 |
| 5,188,673 A |   | 2/1993  | Clausen et al. |
| 5,843,499 A |   | 12/1998 | Moreau et al. |
| 6,262,318 B1 |   | 7/2001  | Heikkila et al. |
| 6,352,845 B1 |   | 3/2002  | Buchanan et al. |

FOREIGN PATENT DOCUMENTS

| GB | 838766 | 6/1960 |
| GB | 850133 | 9/1960 |
| GB | 895145 | 5/1962 |
| WO | WO 00/69280 | 11/2000 |

OTHER PUBLICATIONS

Hicks et al., "Phytosterols and Phytostanols: Functiona Food Cholesterol Busters"Food Technology (2001) 55(1), pp. 63–67, Chicago, IL.
Moreau et al., "Phytosterols in the Auleurone Layer of Corn Kernerls"Biochemical Society Transactions (2000) 28, part 6, pp. 803–806; London, UK.
Singh et al., "Effect of Various Acids and Sulfites in Steep Solution on Yields and Composition of Corn Fiber and Corn Fiber Oil".
Cereal Chem. (2000) 77(5), pp. 665–668; St. Paul, MN.
Hanmaongjai et al., "Enzymatic Process for Extracting Oil and Protein from Rice Bran"(2001) JAOCS, vol. 78, No. 8, pp. 817–821; Champaign, IL.
Moreau et al., "Diferuloylputrescine and p–Coumaroylferu-loylputresceine, Abundant Polyamine Conjugates in Lipid Extracts of Maize Kernels".
Lipids (2001) 36, pp. 839–844; Champaign, IL.
Dunn, "Starch Debranching Without Enzymes: Extrusion and Hydrolysis Effects on Starch Branching", Corn Utilization & Technology Conference, 1998, Program Proceedings, pp. 65–69, published by the Corn Refiners Association and the National Corn Growers Association.
Gulati, et al., "Assessment of ethanol production options for corn products", Bioresource Technology, Dec. 1996, pp 253–264, vol. 58 (No. 3), published by Elsevier Science Ltd.
Grohmann et al., "Saccharification of fiber by combined treatment with dilute sulphuric acid and enzymes", Process Biochemistry (1997), pp. 405–415, vol. 32 (No. 5), published by Elsevier Science Ltd, Barking, London, England.
Knutson et al., "Variations in Enzyme Digestibility and Gelatinization Behavior of Corn Starch Granule Fractions", Cereal Chemistry, 1982, pp. 512–515, vol. 59(No. 5); published by the American Association of Cereal Chemists, Inc. St. Paul, MN.

(Continued)

*Primary Examiner*—James G. Wilson
*Assistant Examiner*—Michael C. Henry
(74) *Attorney, Agent, or Firm*—Wells St. John P.S.

(57) ABSTRACT

The invention includes methods of processing plant material by adding water to form a mixture, heating the mixture, and separating a liquid component from a solid-comprising component. At least one of the liquid component and the solid-comprising component undergoes additional processing. Processing of the solid-comprising component produces oils, and processing of the liquid component produces one or more of glycerol, ethylene glycol, lactic acid and propylene glycol. The invention includes a process of forming glycerol, ethylene glycol, lactic acid and propylene glycol from plant matter by adding water, heating and filtering the plant matter. The filtrate containing starch, starch fragments, hemicellulose and fragments of hemicellulose is treated to form linear poly-alcohols which are then cleaved to produce one or more of glycerol, ethylene glycol, lactic acid and propylene glycol. The invention also includes a method of producing free and/or complexed sterols and stanols from plant material.

19 Claims, 4 Drawing Sheets

OTHER PUBLICATIONS

Ladisch et al., "Process Considerations in the Enzymatic Hydrolysis of Biomass", Enzyme and Microbial Technology, Mar. 1983, pp. 52–102, vol. 5, published by Butterworth & Co. (Publishers) Ltd.

Leathers, "Upgrading Fuel Ethanol Coproducts", Sim News, Sep./Oct. 1988, pp. 210–217, vol. 48 (No. 5), Published by the Society for Industrial Microbiology.

Ning et al., "Modification of Corn Fiber Through Chemical Treatments in Combination with Twin–Screw Extrusion", Cereal Chemistry, 1991, pp. 632–636, vol. 68, No. 6, published by the American Association of Cereal Chemists, Inc., St. Paul, MN.

Saha et al., "Enzymes in Biotechnology", Encyclopedia of Microbiology, vol. 2, 2000, pp. 222–226, Published by Academic Press, Inc.

Saha et al., "Pretreatment and Enzymatic Saccharification of Corn Fiber", Applied Biochemistry and Biotechnology, 1999, pp. 65–77, vol. 76, published by Human Press, Inc.

Saha et al., "Production of Low Cost Sugar from Corn Fiber: Progress, Opportunities and Challenges", Proceedings of the United States–Japan Cooperative Program in Natural Resources (UJNR) Protein Resources Panel, 28th Annual Meeting, Nov. 7–12, Tsujuba, Ibaraki, Japan, 1999, pp. 181–185.

Sanroman et al., "The influence of Substrate on the Kinetics of the Hydrolysis of Starch by Glucoamylase", Applied Biochemistry and Biotechnology, 1996, pp. 329–336, vol. 59, published by Human Press, Inc.

Sims et al., "Hydrolysis of Liquefied Corn Starch in a Membrane Reactor", Biotechnology and Bioengineering, 1992, pp. 960–967, vol. 39, published by John Wiley & Sons, Inc.

Watson et al., "Peripheral Cells of the Endosperms of Grain Sorghum and Corn and their Influence on Starch Purification ", Cereal Chemsitry, 1955, pp. 165–182, vol. 32, No. 3, published by the American Association of Cereal Chemists, Inc., St. Paul, MN.

Watson et al., "Corn: Chemistry and Technology", 1987, pp. 53–82, 253–272, 377–397, published by the American Association of Cereal Chemists, Inc., St. Paul, MN.

Osborn et al., "Corn Hull Hydrolysis Using Glucoamylase and Sulfuric Acid", Starch, vol. 36, No. 11, 1984, pp. 393–395.

Weil, "Pretreatment of Corn Fiber by Pressure Cooking in Water", Applied Biochemistry and Biotechnology, 1998, pp. 1–17, published by Humana Press, Inc.

Wu, "Neural Sugar Contents of Corn Gluten Meal and Corn Gluten Feed", Journal of Agricultural and Food Chemistry, 1996, pp. 136–138, vol. 44, published by the American Chemical Society.

Moreau, et al., "Extraction and Quantitative Analysis of Oil from Commercial Corn Fiber", J. Agric. Food Chem., 1996, J. Agric. Food Chem., 1996, vol. 44, 1996, pp. 2149–2154.

Moreau et al., "Phytosterols and phytostanols lower cholesterol", INFORM, vol. 10, No. 6, Jun. 1999, pp. 572–577.

Moreau et al., "Effect of Heat Pretreatment on the Yield and Composition of Oil Extracted from Corn Fiber", J. Agric. Food Chem., 1999, vol. 47, pp. 2869–2871.

Moreau et al., "Comparison of Yield and Composition of Oil Extracted from Corn Fiber and Corn Bran", Cereal Chem., vol. 76, No. 3, pp. 449–451, 1999.

* cited by examiner

METHODS OF PRODUCING COMPOUNDS FROM PLANT MATERIAL

The invention was made with Government support under Contract DE-FC36-00G10596, A000, awarded by the U.S. Department of Energy. The Government has certain rights in the invention.

TECHNICAL FIELD

The present invention pertains to methods of processing plant material and methods of producing compounds from plant material.

BACKGROUND OF THE INVENTION

Industrial processing of corn material and other plant material currently produces primarily starch with an accompanying large volume of fiber byproduct. Despite the presence of useful components within the fiber byproduct, most of the fiber byproduct is utilized only as a low value component in livestock feed. The usefulness of the plant fiber byproduct is currently limited by a lack of developed methods for processing the plant fiber material to produce the useful compounds contained therein.

It would be desirable to develop methods of producing useful compounds from plant materials.

SUMMARY OF THE INVENTION

In one aspect, the invention encompasses a method of processing plant material. Depending upon the initial water content, an amount of water can be added to the plant material to form a mixture. The mixture is separated into a liquid component and a solid-containing component. At least one of the liquid component and the solid-containing component undergoes additional processing. Processing of the solid component produces oils, and processing of the liquid component produces one or more of ethanol, glycerol, ethylene glycol propylene glycol and lactic acid.

In one aspect, the invention encompasses a process of forming one or more of glycerol, ethylene glycol, lactic acid and propylene glycol from plant matter. Water can be added to plant matter as needed to form a mixture. The mixture is heated and filtered and the filtrate is retained. The filtrate contains hemicellulose, fragments of hemicellulose and starch. At least some of the hemicellulose and fragments of the hemicellulose are converted to diols, linear polyalcohols and/or lactic acid. At least some of the linear polyalcohols are cleaved to produce one or more of glycerol, ethylene glycol, propylene glycol and lactic acid.

In one aspect, the invention encompasses a method of recovering sterols. A material containing plant fiber can be mixed with water to form a mixture. The mixture is heated and filtered to produce a filtrate and a solid-containing portion. The solid-containing portion is treated with one or more solvents to extract a material containing one or more free or complexed sterols, stanols or triglycerides.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

The invention encompasses methods which can be utilized for generating compounds from plant materials. A preliminary processing method encompassed by the present invention is described with reference to FIG. 1. In an initial solubilization step 100 of the preliminary processing, plant material is at least partially is solubilized. In a separation step 200, the plant material solubilized in step 100 is separated into liquid and solid-comprising components.

Step 100 of FIG. 1 is described in greater detail with reference to FIG. 2. The plant material solubilization step 100 initially involves a plant material providing step 110. The plant material provided in step 110 is not limited to a specific plant type and can include, for example, material from one or more of corn, soybean, rice, barley, oats, chicory, wheat, and sugar beet. A mixture comprising the provided plant material and a liquid can be formed in an optional formation step 130. Preferably, step 130 comprises the addition of water to form an aqueous mixture having a final water content of from about 50% to about 90%, by weight. Where the plant material provided in step 110 comprises a water content within the desired range, step 130 can be omitted.

Mixture formation step 130 can comprise forming the mixture to have a pH of from about 1 to about 11, preferably from about 1.5 to about 6.0. Although the pH of the mixture will typically fall within the desired range without adjustment after the addition of water, it is to be understood that the pH of the resulting mixture can be adjusted to fall within this range of pH by addition of one or more of an acid and a base.

Figure 2:
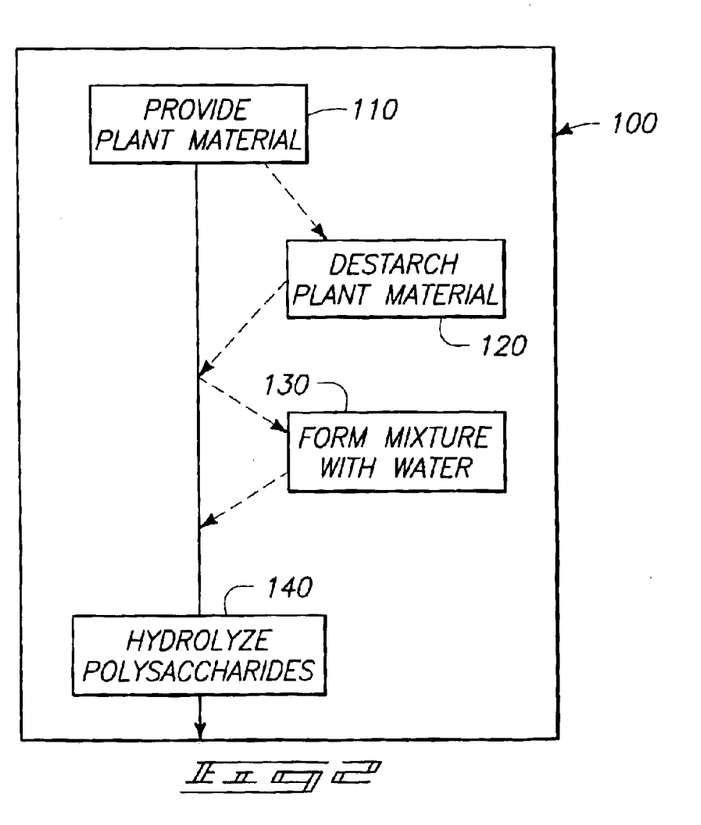
FIG. 2 is a flowchart diagram of step 100 depicted in FIG. 1.

As shown in FIG. 2, providing plant material can optionally comprise destarching the plant material in a destarching step 120. The present invention encompasses methods that utilize both step 120 and step 130, methods that utilize only one of step 120 and step 130, and methods that omit both step 120 and step 130. It is to be understood that methods of the present invention can be used to treat either destarched plant material or plant material that has not undergone a destarching treatment.

For purposes of the present invention, destarched plant material can comprise plant material which has at least some of the original starch content removed. In particular aspects, destarched plant material can have greater than or equal to about 80% of the original starch content removed. Removal of starch from plant material can be achieved by a variety of conventional methods known to those of ordinary skill in the art. After the destarching step 120, the destarched plant material can be used in step 130 to form an aqueous mixture of destarched plant material.

As shown in FIG. 2, a hydrolysis step 140 can be performed during plant material solubilization. Hydrolysis step 140 can hydrolyze at least some of the polysaccharides in the plant material mixture. Hydrolysis step 140 can comprise, for example, heating of the plant material. Step 140 can alternatively or additionally comprise addition of an acid in an amount appropriate to adjust the pH of the mixture to a pH of from about 1 to about 3. Numerous acids are available for use in hydrolysis step 140 such as, for example, sulfuric acid, carbonic acid, phosphoric acid, lactic acid, nitric acid, acetic acid, hydrochloric acid, and mixtures thereof.

In embodiments of the present invention where it is desirable to selectively produce polysaccharides such as, for example, partially-hydrolyzed hemicellulose, it is advantageous to avoid addition of acid or base during solubilization step 100 of the preliminary processing. When the solubilization step 100 is performed utilizing an aqueous mixture comprising a pH between about 1 and about 12 (preferably from about 1.5 to about 6.0), greater than or equal to about 75% of hemicellulose comprised by the mixture can be solubilized while predominantly retaining a polymeric form throughout solubilization step 100.

The plant material mixture formed in step 130 can undergo solubilization from between about 1 minute to about 2 hours, preferably from between about 5 minutes to about 1 hour. Where acid has not been added, the temperature during solubilization can be from about 100° C. to about 200° C., preferably from between about 120° C. to about 180° C., and more preferably from about 140° C. to about 160° C. If acid is added during step 140, the solubilization temperature can be from about 100° C. to about 200° C., preferably from 120° C. to about 180° C., and more preferably from 120° C. to 160° C.

Figure 1:
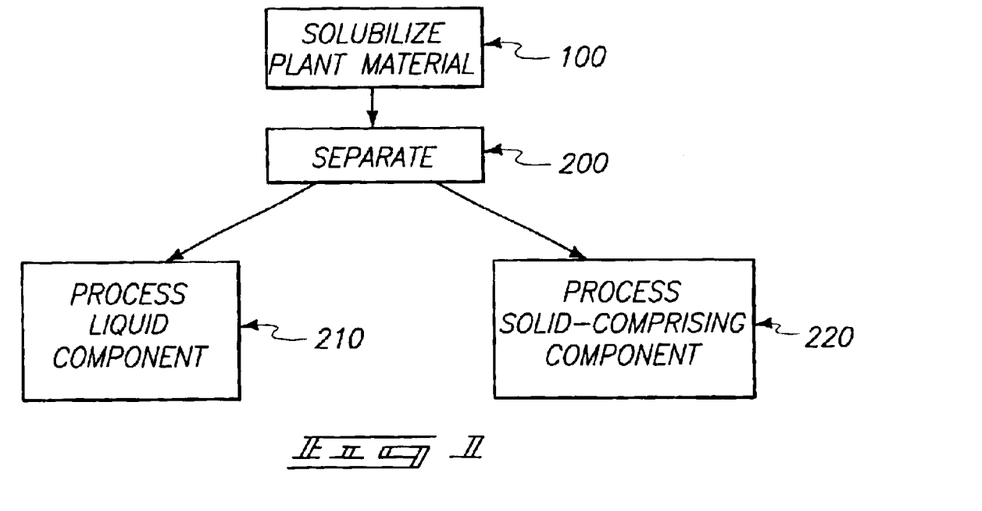
FIG. 1 is a flowchart diagram of a preliminary processing method of the present invention

As shown in FIG. 1, a separation step 200 can be performed after solubilization step 100. Separation step 200 can comprise, for example, one or more of centrifugation, pressing, and filtration. Separation step 200 can produce a liquid-comprising portion or filtrate, and a solid-comprising component. The liquid component 210 and the solid-comprising component 220 can independently undergo further processing as discussed below.

The filtrate or liquid component produced by the separation step 200 can comprise, for example, one or both of polysaccharides and monosaccharides. As discussed above with respect to plant material solubilization step 100 depicted in FIG. 2, the relative amount of monosaccharides and polysaccharides present in the liquid component will depend upon conditions utilized during the solubilization step. The saccharides present in the liquid component can comprise, for example, partially hydrolyzed starch, partially hydrolyzed hemicellulose, polymeric fragments of hemicellulose, and monosaccharide components of hemicellulose. The filtrate can also comprise polysaccharides and monosaccharides of non-hemicellulose origin such as, for example, monosaccharide and polysaccharide breakdown products of starch and cellulose present in the plant material. As shown generally in FIG. 3, liquid component can be subjected to reduction step 400 to chemically reduce at least some of the saccharides present in the filtrate.

Figure 3:
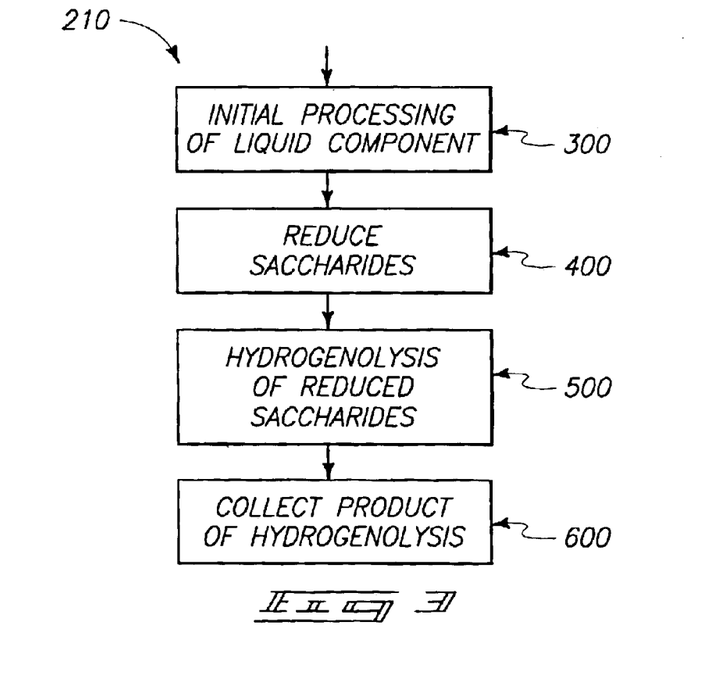
FIG. 3 is a flowchart diagram of a processing method of the present invention.

As indicated generally in FIG. 3, processing of the liquid component 210 can comprise an initial processing step 300 prior to saccharide reduction step 400. Step 300 is described in more detail with reference to FIG. 4. The liquid portion of separation step 200 can be collected in liquid collection step 310 and a neutralization step 320 can be performed if necessary, to adjust the pH of the collected liquid to between about 3 and 8, preferably to a pH of from about 4.5 to about 6.5. Neutralization step 320 can be utilized, for instance, when the preceding processing comprises an addition of acid. It can be advantageous to perform neutralization step 320 prior to a reduction step 400 or a hydrogenolysis step 500 shown in FIG. 3 (discussed below) to alleviate or avoid detrimentally effecting catalyst activity during the reduction or hydrogenolysis.

Figure 4:
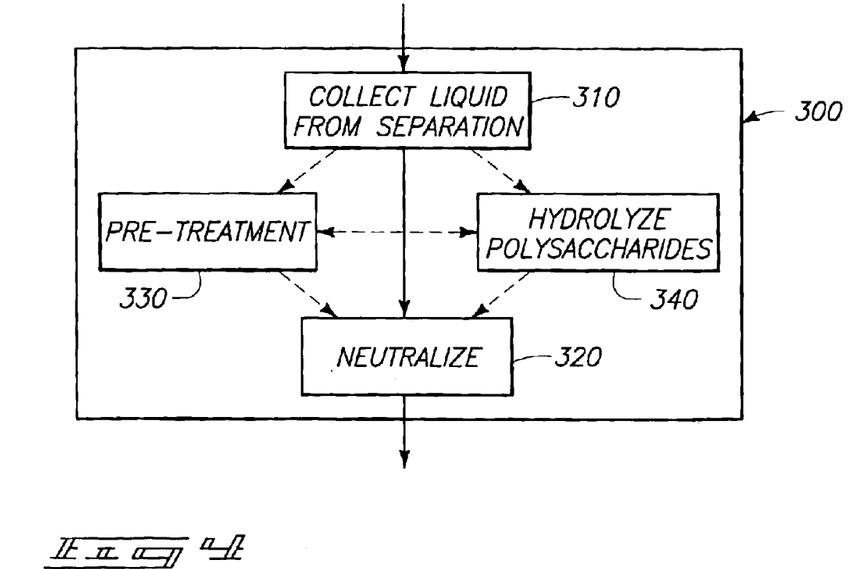
FIG. 4 is a flowchart diagram of step 300 of the processing method shown in FIG. 3.

Referring again to FIG. 4, the liquid collected in step 310 can optionally undergo a pretreatment step 330. As shown in FIG. 4, pretreatment can occur prior to neutralization step 320. Alternatively, pretreatment step 330 can be performed after neutralization step 320. Pretreatment step 330 can comprise, for example, at least one of ultra filtration, carbon filtration, anion exchange chromatography, cation exchange chromatography, and a treatment comprising chemical adjustment followed by precipitation and subsequent separation, where chemical adjustment can include but is not limited to affecting solubility by changing the pH or by addition of a divalent cation. When pretreatment comprises ultra filtration, the ultra filtration can comprise filtration using a molecular weight cutoff filter size of from 2,500 to 50,000. Pretreatment step 330 can remove greater than or equal to 90% of any protein, hydrolyzed protein and/or amino acids present in the liquid solution. It can be advantageous to remove protein from the solution prior to subsequent reduction or hydrogenolysis steps (discussed below) to alleviate or avoid detrimentally effecting or deactivating a catalyst utilized in the reduction or the hydrogenolysis.

In addition to the feature described above, the formation of liquid component step 300 can optionally include a hydrolysis step 340. As shown in FIG. 4, hydrolysis step 340 can be utilized in addition to pretreatment step 330 or can be utilized when pretreatment step 330 is omitted. Where hydrolysis step 340 is utilized in conjunction with pretreatment step 330, hydrolysis step 340 can occur prior to or subsequent to pretreatment step 330. Hydrolysis step 340 can hydrolyze at least some of any polysaccharides present in the liquid collected in step 310. In some instances, it can be advantageous to perform hydrolysis step 340 to hydrolyze polysaccharides present in the solution and thereby minimize any detrimental effect polysaccharides may have on the activity of a catalyst used in subsequent processing steps.

Hydrolysis step 340 can comprise an addition of an acid or a base. Preferably, hydrolysis step 340 utilizes an acid which can comprise, for example, one or more of sulfuric acid, carbonic acid, phosphoric acid, lactic acid, nitric acid, acetic acid, hydrochloric acid, and mixtures thereof. It can be preferable in some instances to use an acid other than sulfuric acid to alleviate detrimental effects sulfate may have on catalysts utilized in subsequent processing steps according to the present invention. In embodiments utilizing acidic hydrolysis step 340, the pH of the solution during the hydrolysis step can preferably be between about pH 1 and about pH 5, and more preferably between about pH 1.5 and pH 2.5.

An effective temperature for purposes of hydrolysis step 340 can be between from about 100° C. to about 200° C., preferably from about 120° C. to about 160° C., and more preferably from between about 120° C. through about 140° C. It can be beneficial to perform hydrolysis step 340 to decrease the high temperature requirements during a subsequent reduction step, discussed below. In embodiments of the present invention where hydrolysis step 340 is utilized, neutralization step 320 can comprise to readjustment of the pH of the liquid to between about 3 and 7, preferably to a pH of from about 4.5 to about 6.5, prior to subsequent processing steps.

Referring again to FIG. 3, initial processing of the liquid component can be followed by reduction step 400. Reduction step 400 can comprise chemical reduction of saccharides by, for example, hydrogenation conditions which can convert at least some of any monosaccharides and polysaccharides present in the liquid component into the respective linear polyalcohols. In addition, if polysaccharides are present in the liquid component, hydrolysis to form the respective monosaccharides can occur during the reduction and can be enhanced by an increased reaction temperature.

Reduction step 400 can comprise catalytic hydrogenation. Catalytic hydrogenation can comprise exposing saccharides to a catalyst comprising a support and one or more members of the groups consisting of Ru, Ni, Pt, and Pd. The catalyst support can comprise carbon and/or other insoluble support material, such as titania and zirconia. Catalytic hydrogenation can comprise a temperature from about 80° C. to about 300° C., preferably from about 100° C. to about 250° C. and more preferably from about 120° C. to about 200° C. A hydrogen pressure during hydrogenation can be from about 100 psig $H_2$ to about 3,000 psig $H_2$, preferably from between about 1,000 psig $H_2$ and about 2,200 psig $H_2$ and most preferably from about 1,200 psig $H_2$ to about 1,800 psig $H_2$. Hydrogenation can be performed over a time range of from about 1 minute to about 8 hours, preferably from between about 1 minute and about 4 hours.

Hydrogenation according to methods of the present invention can produce a total amount of linear polyalcohols which can comprise sorbitol, xylitol and arabinitol as the major polyalcohols present. Sorbitol can comprise from 0% to 100% of the total amount of linear polyalcohols produced, xylitol can comprise from 0% to 100% of the total amount of linear polyalcohols produced, and arabinitol can comprise from 0% to 100% of the total amount of linear polyalcohols produced.

Referring again to FIG. 3, after the reduction of saccharides in reduction step 400, the liquid component can be subjected to a hydrogenolysis step 500. Hydrogenolysis step 500 can cleave at least some of the linear polyalcohols produced by reduction step 400 to form a group of products that can be collected by collection step 600 (discussed below).

Hydrogenolysis step 500 can comprise catalytic hydrogenolysis. Catalytic hydrogenolysis can utilize a catalyst such as, for example, a catalyst comprising a support and one or more members of the group consisting of Ru, Ni, Re, and Co. The support can comprise for example, one or more of carbon, titania and zirconia. Catalytic hydrogenolysis step 510 can further comprise utilization of an added base. Assuming a neutral starting pH of from about pH 5 to about pH 8, an appropriate pH for catalytic hydrogenolysis step 510 can be achieved by, for example, an addition sodium hydroxide to a final concentration of from about 0% to about 10% by weight, and preferably from about 0.5% to about 2% by weight, relative to the weight of the final solution.

As shown in FIG. 3, reduction reaction step 400 and hydrogenolysis reaction step 500 can be performed individually. Alternatively, the reduction reaction can be combined with hydrogenolysis within a common reaction vessel (not shown) and can utilize a common catalyst. For purposes of a combined hydrogenation/hydrogenolysis, a common catalyst can be, for example, Ru on a carbon support. The conditions for the combined hydrogenation and hydrogenolysis reactions can comprise initial conditions identical to the conditions discussed above with respect to reduction reaction 400 as conducted independently. In the combined reaction, hydrogenolysis can be induced by, for example, an addition of sodium hydroxide into the common reaction chamber. Assuming the solution was neutralized prior to the hydrogenation conditions, sodium hydroxide can be added according to the conditions discussed above with respect to hydrogenolysis reaction step 500, as conducted independently. The appropriate amount of sodium hydroxide to be utilized for hydrogenolysis reaction, either as performed independently or as combined with reduction reaction 400, can be varied within the ranges discussed above based upon the pH of the solution prior to addition of the base and the sugar concentration in the solution.

As shown in FIG. 3, a product collection step 600 can be performed after hydrogenolysis reaction 500 to collect a group of products. The group of products can comprise one or more of lactic acid, propylene glycol, ethylene glycol and glycerol. A combined amount of ethylene glycol, propylene glycol and glycerol in the liquid component after hydrogenolysis reaction 500 can comprise from about 50% to about 100% of the total amount of carbon present in the liquid component.

In addition to the features described above, methods of the present invention can include processing of a solid-comprising portion 220 obtained by the separation step 200 shown in FIG. 1. Methods for processing of the solid-comprising portion according to the present invention are discussed generally with reference to FIG. 5. An initial processing step 700 can optionally be utilized to remove at least some of any liquid portion present in the solid-comprising component. Initial processing step 700 can comprise removal of some or all of any water present in the component utilizing one or more of filtration, air drying, vacuum drying and heating. Alternatively, subsequent processing of the solid-comprising component can be performed in an absence of any further removal of liquid or additional drying.

Figure 5:
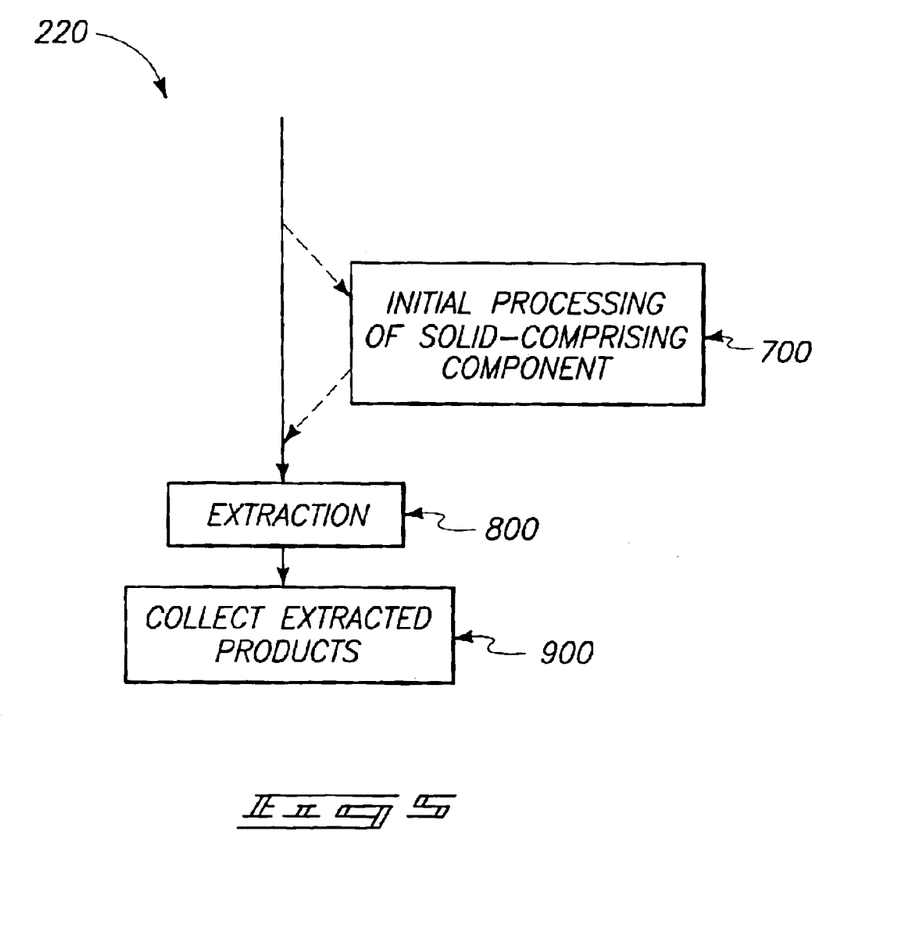
FIG. 5 is a flowchart diagram of a particular processing sequence of the present invention.

As shown in FIG. 5, whether or not initial processing step 700 is performed, processing of the solid-comprising component can include an extraction step 800. Extraction step 800 is discussed in more detail with reference to FIG. 6. Extraction step 800 can include a first solvent addition step 810. Numerous suitable solvents are available for purposes of the extraction step, and can include but are not limited to one or more of hexane, ethyl acetate, methylene chloride, and acetone. Solvent can be added to provide a volume to mass ratio of from about 1:1 to about 20:1, where the volume is the volume of the added solvent and the mass is the mass of the solid-comprising component prior to solvent addition. In particular processing events, the volume to mass ratio can preferably be about 10:1. The extraction can be conducted for a time of from a few seconds to several hours. Additionally, the extraction can be conducted batchwise or utilizing a continuous process. Extraction step 800 can comprise a first solvent separation step 820 to separate the first solvent from a non-solubilized portion of the solid component. A collection step 830 can be utilized to collect a solubilized component in the separated first solvent.

Figure 6:
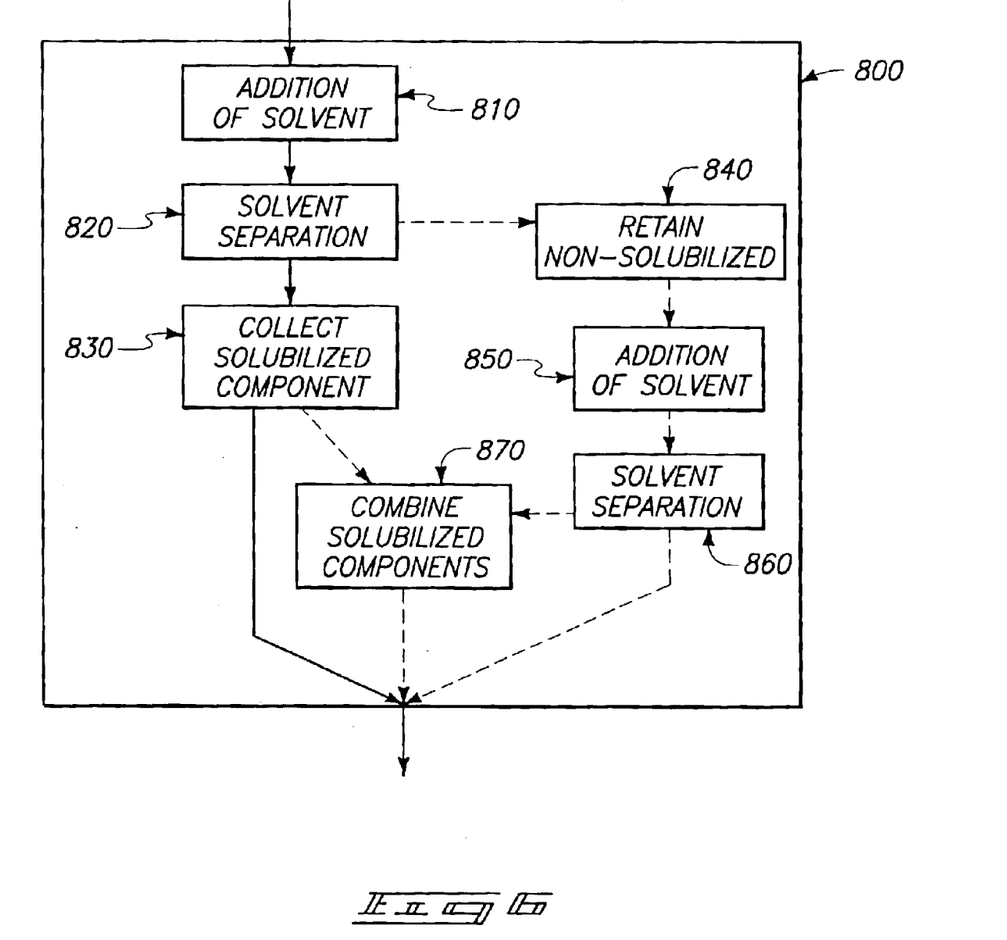
FIG. 6 is a flowchart diagram of step 800 of the processing sequence shown in FIG. 5.

As shown in FIG. 6, the non-solubilized portion of solvent separation step 820 can be retained in a retention step 840. An optional second solvent addition step 850 can be performed and can utilize the conditions discussed above with respect to the first solvent addition. After a second solvent addition, a second solvent separation step 860 can be performed and the second solvent portion containing a second solubilized component can be recovered. The second solubilized component can be combined with the first solubilized component in a combination step 870 which combines the solvent collected in step 830 with the solvent collected from separation step 860. Alternatively the first solvent collected in 830 and the second solvent collected in 860 can remain separate. It is to be noted that the solvent used for addition of solvent step 810 and the solvent used for the second solvent addition step 850 can be identical or can be different. Further, the first solvent collected in step 830 can comprise a product material that is different than the product material extracted by the second solvent addition.

As shown in FIG. 6, extraction step 800 can comprise one or two additions of solvent steps 810 and 850. It is to be understood that the present invention can encompass methods utilizing greater than two solvent addition steps (not shown). It can be advantageous to utilize a plurality of solvent additions and separation steps to maximize product extraction.

Referring again to FIG. 5, after extraction step 800, the extracted products can be collected in a collection step 900. The extracted products collected in step 900 can be from about 3% to about 5% of the initial plant material by weight, or alternatively up to 100% of available extractables. The extracted product can comprise, for example, one or more of campesterol, campestanol, stigmasterol, sitosterol, sitostanol, tocopherols and triglycerides.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method of extracting compounds from plant material, comprising:

providing plant material;

solubilizing the plant material to form a mixture having a pH of from about 3 to about 9, the mixture comprising a solubilized fraction and a non-solubilized fraction, the solubilized fraction comprising an extracted amount of starch and an extracted amount of hemicellulose, the solubilizing comprising adding water to the plant material to form the mixture;

separating the solubilized fraction from the non-solubilized fraction; and chemically reducing at least a portion of the extracted amount of starch and the extracted amount of hemicellulose in the solubilized fraction.

2. The method of claim 1 wherein the plant material comprises an initial amount of starch and an initial amount of hemicellulose prior to the solubilizing; wherein the extracted amounts of starch and hemicellulose consist of partially-hydrolyzed starch, partially-hydrolyzed hemicellulose and hydrolyzed hemi-cellulose; and wherein the solubilized fraction comprises from about 40% to about 100% of the initial amount of hemi-cellulose, and from about 40–100% of the initial amount of starch.

3. The method of claim 2 wherein the extracted amount of hemicellulose comprises greater than about 40% partially-hydrolyzed hemicellulose.

4. The method of claim 1 wherein the plant material comprises one or more of corn material, soy bean material, rice material, barley material, oat material, chicory material, wheat material, and sugar beet material.

5. The method of claim 1 wherein the separating comprises at least one of filtering, pressing and centrifugation.

6. The method of claim 1 wherein the plant material comprises destarched plant material, destarched plant material being plant material having at least about 80% of the original starch content removed.

7. The method of claim 1 wherein the solubilizing comprises heating from about 100° C. to about 200° C.

8. The method of claim 1 further comprising, after collecting the solubilized fraction, hydrolyzing at least some of the extracted hemicellulose by adjusting the pH to a pH above about 8 or to a pH of below about 3.

9. The method of claim 1 further comprising, prior to chemically reducing, performing a pro-treatment comprising one or more of ultra-filtration, carbon filtration, precipitation, anion exchange chromatography, and cation exchange chromatography.

10. The method of claim 1 wherein the chemically reducing comprises hydrogenation in the presence of a catalyst.

11. The method of claim 10 wherein the catalyst comprises a support and at least one of Ni, Ru, Re, Pt, Pd and Co, the support comprising at least one of carbon, titania, and zirconia.

12. The method of claim 11 wherein the catalyst comprises Ru.

13. The method of claim 1 wherein the chemically reducing converts at least some of the starch, starch fragments, hemicellulose and fragments of hemicellulose, to corresponding linear poly-alcohols.

14. The method of claim 1 wherein the chemically reducing results in the production of one or more linear poly-alcohols selected from the group consisting of sorbitol, xylitol and arabinitol.

15. The method of claim 1 further comprising hydrogenolysis of at least a portion of the solubilized fraction.

16. The method of claim 15 wherein the hydrogenolysis occurs after the chemically reducing.

17. The method of claim 15 wherein the chemically reducing and the hydrogenolysis occur in a common reaction vessel.

18. The method of claim 17 wherein a base is added to the common reaction vessel.

19. The method of claim 17 wherein the hydrogenolysis and the chemically reducing are catalyzed by a common catalyst comprising a support and a member of the group consisting of Ru, Ni/Re, Co/Re and Ru/Re, the support comprising one or more of carbon, titania and zirconia.

\* \* \* \* \*

UNITED STATES PATENT AND TRADEMARK OFFICE
CERTIFICATE OF CORRECTION

PATENT NO. : 6,982,328 B2 Page 1 of 1
APPLICATION NO. : 10/379299
DATED : January 3, 2006
INVENTOR(S) : Todd A. Werpy et al.

It is certified that error appears in the above-identified patent and that said Letters Patent is hereby corrected as shown below:

Column 1, line 39 - After "ethylene glycol" insert --,--.

Column 2, line 18 - Delete "is" after "partially".

Column 2, line 29 - After "optional" insert --mixture--.

Column 5, line 51 - After "addition" insert --of--.

Column 8, line 22 - Delete "pro-treatment-- and insert --pre-treatment--.

Signed and Sealed this

Seventeenth Day of October, 2006

JON W. DUDAS
*Director of the United States Patent and Trademark Office*